United States Patent [19]

Jiang et al.

[11] Patent Number: 5,360,818
[45] Date of Patent: Nov. 1, 1994

[54] 1,3-DIOXANE DERIVATIVES HAVING PROTEIN KINASE C INHIBITORY ACTIVITY

[75] Inventors: Jack B. Jiang, Chapel Hill; Mary G. Johnson; Jeffrey Nichols, both of Durham, all of N.C.

[73] Assignee: Sphinx Pharmaceuticals Corporation, Durham, N.C.

[21] Appl. No.: 110,847

[22] Filed: Aug. 24, 1993

Related U.S. Application Data

[63] Continuation of Ser. No. 763,622, Sep. 23, 1991, abandoned.

[51] Int. Cl.$^5$ .................. A61K 31/35; C07D 309/14
[52] U.S. Cl. .................................... 514/459; 549/371
[58] Field of Search ....................... 549/371; 514/459

[56] References Cited

U.S. PATENT DOCUMENTS

| | | |
|---|---|---|
| 2,254,876 | 9/1941 | Senkus . |
| 2,568,555 | 9/1951 | Moore . |
| 2,882,275 | 4/1959 | Meiser et al. . |
| 3,060,196 | 10/1962 | Grob . |
| 3,459,771 | 8/1969 | Hitz et al. . |
| 3,621,033 | 11/1971 | Houlihan . |
| 4,816,450 | 3/1989 | Bell et al. . |

OTHER PUBLICATIONS

Braun, C. E., J. Amer. Chem. Soc. 55: 1280–1285 (1933).
Castagna et al., J. Biol. Chem. 257: 7847, 1982.
Grunicke et al., Adv. Enzyme Regul. 28: 201, 1989.
Tritton et al., Cancer Cells 2: 95–102, 1990.
Schachtele et al., Biochem. Biophy. Res. Commun. 151: 542, 1988.
Hannun et al., J. Biol. Chem. 262: 13620, 1987.
Yamada et al., Biochem. Pharmacol. 37: 1161, 1988.
McIntyre et al., J. Biol. Chem. 262: 15730, 1987.
Lambreth et al., J. Biol. Chem. 263: 3818, 1988.
Pittet et al., J. Biol. Chem. 262: 10072, 1987.
Gaudry et al., Immunology 63: 715, 1988.
Wilson et al., J. Biol. Chem. 261: 12616, 1986.
Fujita et al., Biochem. Pharmacol. 35: 4555, 1986.
Berkow et al., J. Leukoc. Biol. 41: 441, 1987.
Salzer et al., Biochem. Biophys. Res. Commun. 148: 747, 1987.
Kramer et al., J. Biol. Chem. 262: 5876, 1989.
Dewald et al., Biochem. J. 264: 879, 1989.

(List continued on next page.)

*Primary Examiner*—Nicky Chan
*Attorney, Agent, or Firm*—Woodcock Washburn Kurtz Mackiewicz & Norris

[57] ABSTRACT

The present invention provides compounds having the formula

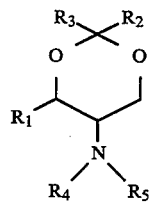

wherein $R_1$ is alkyl, alkenyl and alkynyl having from 2 to about 20 carbon atoms; $R_2$, $R_3$ and $R_6$ are independently H, phenyl or alkyl having from 1 to about 20 carbon atoms; and $R_4$ and $R_5$ are independently H, $R_6$imino, or amidino, and pharmaceutically acceptable salts thereof which are useful for inhibiting protein kinase C and treating conditions related to, or affected by inhibition of protein kinase C, particularly cancer tumors, inflammatory disease, reperfusion injury, and cardiac dysfunctions related to reperfusion injury.

16 Claims, No Drawings

OTHER PUBLICATIONS

Stoffel et al., Hoppe–Seyler's Z. Physiol. Chem., 348: 1561–69, 1967.
Gigg and Warren, J. Chem. Soc. (C), 2661, 1968.
Eliel et al., J. Org. Chem., 42(9): 1533, 1977.
Kaloustian et al., J. Am Chem. Soc. 98(4): 956, 1976.
Mori et al., Tetrahedron Letters, 22(44): 4429, 1981.
Saitoh et al., Bull. Chem. Soc. Jpn., 54: 488, 1981.
Garner et al., J. Org. Chem. 52(12) 2361, 1987.
Hino et al., J. Chem. Soc. Perkin Trans. I: 1687, 1986.
Kiso et al., Carbohydrate Res., 158: 101–111, 1986.
Herold, Helvetica Chimica ACTA, 71: 354, 1988.
Ohashi et al., Tetrahedron 45(9): 2557, 1989.
Nakagawa et al., J. Chem. Soc., Chem. Commun. 603–605, 1990.
Umemura and Mori, Agric. Biol. Chem., 46(7): 1797, 1982.
Nakagawa et al., Tetrahedron Letters 28(50): 6281, 1987.
Kodato et al., Tetrahedron 45(23): 7263, 1989.
Merck Index, 10th edition, Merck & Co., Inc., Rahway, N.J., 1983, p. 869.

1,3-DIOXANE DERIVATIVES HAVING PROTEIN KINASE C INHIBITORY ACTIVITY

This is a continuation of application Ser. No. 07/763,622, filed Sep. 23, 1991, now abandoned.

FIELD OF THE INVENTION

The present invention relates to diagnosis and treatment of inflammatory, cardiovascular and neoplastic diseases. More particularly, the present invention relates to 1,3-dioxane derivatives for inhibiting activity of the enzyme protein kinase C family of enzymes in mammals.

BACKGROUND OF THE INVENTION

Protein kinase C (PKC) is a family of calcium- and phospholipid-dependent serine/threonine-specific protein kinases which play an important role in cellular growth control, regulation, and differentiation. Protein kinase C is also fundamental to the processes involved in tumorigenicity, since it is the major high-affinity receptor for several classes of tumor promoters as well as for endogenous cellular diacylglycerols. These tumor promoters also stimulate protein kinase C catalysis. Castagna et al., *J. Biol. Chem.* 257: 7847, 1982 reported direct activation of protein kinase C by tumor promoting phorbol esters. Mechanisms of protein kinase C action have been described in U.S. Pat. No. 4,816,450 issued Mar. 28, 1989 to Bell et al., the disclosures of which are incorporated as if fully set forth herein. Protein kinase C is activated by diacylglycerol (DAG), a neutral lipid, and when activated will transfer the γ-phosphate of MgATP to a serine or threonine residue on a substrate protein.

Since the activation of protein kinase C has been implicated in several human disease processes, including cancer tumors, inflammation, and reperfusion injury, inhibition of protein kinase C should be of great therapeutic value in treating these conditions.

Certain protein kinase C inhibitors have been reported to potentiate the antitumor activity of cis-platin both in vitro and in vivo. See Grunicke et al., *Adv. Enzyme Regul.* 28: 201, 1989; and German Offenlegungsschrift DE 3827974. In addition, it has been suggested that protein kinase C would be a potential target for therapeutic design because of its central role in cell growth. See Tritton, T. R. and Hickman, J. A. *Cancer Cells* 2: 95-102, 1990. Further, inflammation and reperfusion injury, particularly pertaining to cardiac injury, are common conditions for which there exists no definitive treatment despite extensive research, and appropriate treatments for these conditions are needed.

Certain protein kinase C inhibitors have been demonstrated to block platelet aggregation and release of neutrophil activating agents such as platelet activating factor, PAF. See Schachtele et al., *Biochem. Biophy. Res. Commun.* 151: 542, 1988; Hannun et al., J. Biol. Chem. 262: 13620, 1987 and Yamada et al., *Biochem. Pharmacol.* 37: 1161, 1988. Protein kinase C inhibitors have also been shown to inhibit neutrophil activation, and chemotactic migration. See McIntyre et al., *J. Biol Chem.* 262: 15730, 1987; Lambreth et al., *J. Biol. Chem.* 263: 3818, 1988; Pittet et al., *J. Biol. Chem.* 262: 10072, 1987; and Gaudry et al., *Immunology* 63: 715, 1988. Further, protein kinase C inhibitors have been shown to inhibit neutrophil degranulation and release of proteolytic enzymes and reactive oxygen intermediates. See Wilson et al., *J. Biol. Chem.* 261: 12616, 1986; Fujita et al., *Biochem. Pharmacol.* 35: 4555, 1986; Berkow et al., *J. Leukoc. Biol.* 41: 441, 1987; Salzer et al., *Biochem. Biophys. Res. Commun.* 148: 747, 1987; Kramer et al., *J. Biol. Chem.* 262: 5876, 1989; and Dewald et al., *Biochem. J.* 264: 879, 1989.

It is apparent that inhibitors of protein kinase C have the potential for blocking all three of the most significant mechanisms of pathogenesis associated with myocardial reperfusion injury, and should thus have a decided therapeutic advantage. Additionally, the inhibitory effect of protein kinase C inhibitors on keratinocytes, and on the oxidative burst in neutrophils will lead to an anti-inflammatory effect.

German Offenlegungsschrift DE 3827974 A1 discloses therapeutic preparations comprising a protein kinase C inhibitor in combination with a lipid, a lipid analog, a cytostatic agent or phospholipase inhibitor useful for cancer therapy. However, none of the protein kinase C inhibitors disclosed in this publication are 1,3-dioxanes.

Substituted 1,3-dioxanes have been reported for antifungal, antibacterial and antiviral uses (Houlihan, U.S. Pat. No. 3,621,033 issued Nov. 16, 1971, Meiser, et al., U.S. Pat. No. 2,882,275 issued Apr. 14, 1959, and Moore, U.S. Pat. No. 2,568,555 issued Sep. 18, 1951), and agricultural uses (Hitz, et al., U.S. Pat. No. 3,459,771 issued Aug. 5, 1969). 1,3 dioxanes have been reported in research on sphingolipid synthesis and biochemistry. See Stoffel et al., Hoppe-Seyler's *Z. Physiol. Chem.*, 348: 1561-69, 1967; Gigg and Warren, *J. Chem. Soc.*(C), 2661, 1968; Eliel et al., *J. Org. Chem.* 42(9): 1533, 1977; Kaloustian et al., *J. Am. Chem. Soc.* 98 (4): 956, 1976; Mori et al., *Tetrahedron Letters,* 22 (44): 4429, 1981; Saitoh et al., *Bull. Chem. Soc. Jpn.,* 54: 488, 1981; Garner et al., *J. Org. Chem.* 52(12): 2361, 1987; Hino et al., *J Chem. Soc. Perkin Trans. I:* 1687, 1986; Kiso et al., *Carbohydrate Res.,* 158: 101-111, 1986; Herold, *Helvetica Chimica ACTA,* 71: 354, 1988; Ohashi et al., *Tetrahedron* 45(9): 2557, 1989; and Nakagawa et al., *J. Chem. Soc., Chem. Commun.* 603-605, 1990. 1,3-dioxanes have also been reported as intermediates in organic syntheses of other types of compounds. See Umemura and Mori, *Agric. Biol. Chem.,* 46(7): 1797, 1982; Nakagawa et al., *Tetrahedron Letters* 28(50): 6281, 1987; Kodato et al., *Tetrahedron* 45(23): 7263, 1989; and Grob, et al., U.S. Pat. No. 3,060,196 which discloses 1,3-dioxane intermediates used in synthesis of unsaturated aliphatic aminodiols.

Diagnosis and treatment for inflammatory, cardiovascular and neoplastic diseases are critical medical needs. Moreover, there exists no definitive treatment for inflammation and reperfusion injury, particularly pertaining to cardiac injury, despite extensive research. Appropriate treatments for these conditions are needed. Thus, there remains a long-felt need for efficacious inhibitors of protein kinase C for therapeutic use.

SUMMARY OF INVENTION

The present invention provides compounds having formula I below:

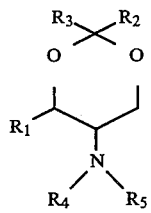

Formula I wherein $R_1$ is alkyl, alkenyl or alkynyl having from 2 to about 20 carbon atoms; $R_2$, $R_3$, $R_6$ are independently H, phenyl or alkyl having from 1 to about 20 carbon atoms; and $R_4$ and $R_5$ are H, $R_6$imino, or amidino, at least one of $R_4$ and $R_5$ being $R_6$imino, or amidino, and pharmaceutically acceptable salts thereof.

The invention also provides compounds of formula I wherein $R_1$ is alkyl, alkenyl or alkynyl having from 2 to about 20 carbon atoms; $R_2$ is alkyl having from 1 to 5 carbon atoms and $R_3$ is H, or $R_3$ is alkyl having from 1 to 5 carbon atoms and $R_2$ is H; $R_4$ and $R_5$ are independently H, $R_6$imino, or amidino, and $R_6$ is independently H, phenyl or alkyl having from 1 to about 20 carbon atoms, and pharmaceutically acceptable salts thereof.

The present invention further provides compounds of formula I wherein $R_1$ is alkyl, alkenyl or alkynyl having from 2 to about 20 carbon atoms; $R_2$ is alkyl having from 7 to 20 carbon atoms and $R_3$ is H, or $R_3$ is alkyl having from 7 to 20 carbon atoms and $R_2$ is H; $R_4$ and $R_5$ are independently H, $R_6$imino, or amidino, and $R_6$ is independently H, phenyl or alkyl having from 1 to about 20 carbon atoms, and pharmaceutically acceptable salts thereof.

The invention additionally provides compounds of formula I wherein $R_1$ is alkyl having from 2 to about 20 carbon atoms, or alkenyl or alkynyl having from 2 to 14 carbon atoms; $R_2$ is phenyl; $R_3$ and $R_6$ are independently H, or alkyl having from 1 to about 20 carbon atoms; and $R_4$, $R_5$ are H, $R_6$imino, or amidino, and pharmaceutically acceptable salts thereof.

The compounds of the invention inhibit protein kinase C and exert anti-inflammatory, anti-cancer, and reperfusion injury protection effects through their anti-proliferative and anti-inflammatory activities in human neutrophils and tumor cells. Also within the scope of the invention are the pharmaceutically acceptable salts and the optically active stereoisomers of the compounds of the invention.

The present invention also provides novel methods useful for treating conditions related to, or affected by inhibition of protein kinase C activity, particularly cancer tumors, inflammatory disease, reperfusion injury, and cardiac dysfunctions related to reperfusion injury. A compound having the formula (formula I)

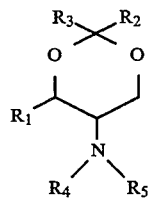

wherein $R_1$ is alkyl, alkenyl and alkynyl having from 2 to about 20 carbon atoms; $R_2$, $R_3$ and $R_6$ are independently H, phenyl or alkyl having from 1 to about 20 carbon atoms; and $R_4$ and $R_5$ are independently H, $R_6$imino, or amidino is administered to the mammal or cells in amounts effective to inhibit protein kinase C, or ameliorate the condition for which is administered.

Another aspect of the present invention provides pharmaceutical compositions comprising a pharmaceutically acceptable carrier or diluent and a compound of formula I wherein $R_1$ is alkyl, alkenyl and alkynyl having from 2 to about 20 carbon atoms; $R_2$, $R_3$ and $R_6$ are independently H, phenyl or alkyl having from 1 to about 20 carbon atoms; and $R_4$ and $R_5$ are independently H, $R_6$imino, or amidino, and pharmaceutically acceptable salts thereof.

This invention is more particularly pointed out in the appended claims and is described in its preferred embodiments in the following description.

DETAILED DESCRIPTION OF THE INVENTION

The present invention provides 1,3-dioxanes, and their pharmaceutically acceptable salts that have protein kinase C inhibiting activity, and exert anti-inflammatory, anti-cancer, and reperfusion injury protection effects through their anti-proliferative and anti-inflammatory activities in human neutrophils and tumor cells. The compounds and pharmaceutical compositions of the invention are useful for treating conditions related to, or affected by inhibitions of protein kinase C activity, particularly cancer tumors, inflammatory disease, reperfusion injury, and cardiac dysfunctions related to reperfusion injury. The compounds useful in the methods of the invention are selective for protein kinase C and have no effect on cyclic AMP (cAMP) dependent protein kinase activity. The compounds useful in the invention should thus have no effect on the metabolic pathways associated with stimulation of protein kinase by cAMP. The compounds useful in the invention not only inhibit tumor cell proliferation but are not cross-resistant to the multi-drug-resistant family of agents such as adriamycin.

The present invention provides 1,3 dioxanes having the following formula (formula I):

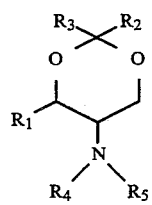

wherein $R_1$ is preferably alkyl, alkenyl or alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are preferably independently H, phenyl or alkyl having from 1 to about 20 carbon atoms, more preferably independently H or alkyl having from 1 to 5 carbon atoms, most preferably independently H, methyl or ethyl; and $R_4$ and $R_5$ are H, $R_6$imino, or amidino, more preferably H or $R_6$imino, at least one of $R_4$ and $R_5$ being $R_6$imino, or amidino, and pharmaceutically acceptable salts thereof.

The invention also provides other 1,3-dioxanes having formula I wherein $R_1$ is alkyl, alkenyl or alkynyl having from 2 to about 20 carbon atoms, more preferably alkyl, alkenyl or alkynyl having from about 10 to about about 20 carbon atoms, most preferably alkyl, alkenyl or alkynyl having from about 15 to about 20 carbon atoms; $R_2$ is alkyl having from 1 to 5 carbon atoms and $R_3$ is H, or $R_3$ is alkyl having from 1 to 5 carbon atoms and $R_2$ is H; $R_4$ and $R_5$ are independently H, $R_6$imino, or amidino, and $R_6$ is independently H, phenyl or alkyl having from 1 to about 20 carbon atoms, and pharmaceutically acceptable salts thereof. A preferred compound of the invention has the structure of formula I wherein $R_1$ is alkyl having 15 carbon atoms, $R_2$ is methyl, $R_3$ is H, $R_4$ is H and $R_5$ is H.

The present invention further provides 1,3-dioxanes having the structure of formula I wherein $R_1$ is alkyl, alkenyl or alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$ is alkyl having from 7 to 20 carbon atoms and $R_3$ is H, or $R_3$ is alkyl having from 7 to 20 carbon atoms and $R_2$ is H; $R_4$ and $R_5$ are independently H, $R_6$imino, or amidino, and $R_6$ is H, phenyl or alkyl having from 1 to about 20 carbon atoms, and pharmaceutically acceptable salts thereof.

The invention additionally provides 1,3-dioxanes having the structure of formula I wherein $R_1$ is alkyl having from 2 to about 20 carbon atoms, or alkenyl or alkynyl having from 2 to 14 carbon atoms; $R_2$ is phenyl; $R_3$ and $R_6$ are independently H, or alkyl having from 1 to about 20 carbon atoms; and $R_4$ and $R_5$ are H, $R_6$imino, or amidino, and pharmaceutically acceptable salts thereof.

Preferred compounds of the invention are shown in Table 1.

The pharmaceutical compositions of the invention comprise a pharmaceutically acceptable carrier or diluent and a compound of formula I wherein $R_1$ is alkyl, alkenyl or alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof.

The present invention thus provides methods for inhibiting protein kinase C which comprise contacting protein kinase C with an inhibitory amount of a compound having the formula

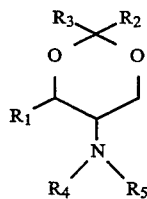

wherein $R_1$ is alkyl, alkenyl or alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention.

Another aspect of the invention provides methods of inhibiting an oxidative burst in neutrophils which comprises contacting a neutrophil with an amount of a compound having the structure of formula I wherein $R_1$ is alkyl, alkenyl and alkynyl having from 2 to about 20 carbon atoms more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention effective to inhibit such oxidative burst, or contacting a neutrophil with a protein kinase C inhibitory concentration of such compound or pharmaceutical composition. As used herein, the term "protein kinase C inhibitory concentration" refers to the concentration of a compound that will inhibit protein kinase C activity.

A further aspect of the invention provides methods for treating inflammation which comprises administering to a mammal suffering from inflammation an amount of a compound having the structure of formula I wherein $R_1$ is alkyl, alkenyl and alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention effective to inhibit inflammation, or administering to the mammal a protein kinase C inhibitory concentration of such or pharmaceutical composition of the invention.

Another aspect of the invention provides a method for inhibiting growth of mammalian tumor cells which comprises contacting a mammalian tumor cell with a protein kinase C inhibitory concentration of a compound having the structure of formula I wherein $R_1$ is alkyl, alkenyl and alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention, or contacting the tumor cell with an amount of such compound or pharmaceutical composition of the invention effective to inhibit growth of the tumor cell.

Yet another aspect of the invention provides methods treating mammalian tumors which comprises administering to a mammal having a tumor a protein kinase C inhibitory concentration of a compound having the structure of formula I wherein $R_1$ is alkyl, alkenyl and alkynyl having from 2 to about 20 carbon atoms more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention, or contacting the tumor cell with an amount of a compound of such invention or pharmaceutical composition of the invention effective to inhibit growth of the tumor.

Still another aspect of the invention provides methods of inhibiting keratinocyte proliferation comprising administering to a keratinocyte a protein kinase C inhibitory amount of a compound having the structure of formula I wherein $R_1$ is alkyl, alkenyl and alkynyl having from 2 to about 20 carbon atoms, more preferably alkyl, alkenyl or alkynyl having from about 10 to about 20 carbon atoms, most preferably alkyl, alkenyl or alkynyl having from about 15 to about 20 carbon atoms; $R_2$, $R_3$ and $R_6$ are independently H, phenyl or alkyl having from 1 to about 20 carbon atoms, more preferably independently H, phenyl or alkyl having from 1 to about 5 carbon atoms, most preferably independently H, methyl or ethyl; and $R_4$ and $R_5$ are independently H, $R_6$imino, or amidino, more preferably independently H or $R_6$imino, or pharmaceutically acceptable salt thereof, or a pharmaceutical composition of the invention, or contacting a keratinocyte with an amount of such compound or a pharmaceutical composition of the invention effective to inhibit proliferation of the keratinocyte.

The compounds and pharmaceutical compositions of the invention may be administered by any method that produces contact of the active ingredient with the agent's site of action in the body of a mammal, or in the body fluid or tissue including but not limited to oral, topical, hypodermal, intramuscular, intravenous, and intraparenteral. The compounds may be administered singly, or in combination with other compounds of the invention, other pharmaceutical compounds, such as chemotherapeutic compounds, or in conjunction with therapies, such as radiation treatment. 1,3 dioxane derivatives are preferably administered with a pharmaceutically acceptable carrier selected on the basis of the selected route of administration and standard pharmaceutical practice.

The compounds are administered to mammals, preferably humans, in therapeutically effective amounts which are effective to inhibit protein kinase C, or to inhibit tumor cell growth, inhibit inflammation of tissue, inhibit keratinocyte proliferation, inhibit oxidative burst from neutrophils or inhibit platelet aggregation. The dosage administered in any particular instance will depend upon factors such as the pharmacodynamic characteristics of the particular compound, its mode and route of administration, the age, health, and weight of the recipient, the nature and extent of symptoms, kind of concurrent treatment, frequency of treatment, and the effect desired.

Pharmaceutically acceptable salts of the compounds useful in the present invention and pharmaceutical compositions of the invention are also within the scope of the invention. Such pharmaceutically acceptable salts useful in the invention include hydrochloride, hydrobromide, succinate, fumarate, oxalate, methanesulfonate, sulfate, maleate, malonate, acetate or lactate. It is contemplated that the daily dosage of the compounds will be in the range of from about 0.1 to about 40 mg per kg of body weight, preferably from about 1 to about 20 mg per kg body weight. The pharmaceutical compositions of the invention may be administered in any dosage form, including a single dosage, divided dosages, or in sustained release form. Persons of ordinary skill will be able to determine dosage forms and amounts with only routine experimentation based upon the considerations of the invention. Isomers of the compounds and pharmaceutical compositions, particularly optically active stereoisomers, are also within the scope of the present invention.

The pharmaceutical compositions of the invention may also be administered orally in solid dosage forms, such as capsules, tablets, and powders, or in liquid dosage forms, such as elixirs, syrups, and suspensions. They may also be administered parenterally in sterile liquid dosage forms or topically in a carrier. The pharmaceutical compositions of the invention may be formulated into dosage forms according to standard practices in the field of pharmaceutical preparations. See *Remington's Pharmaceutical Sciences*, A. Osol, Mack Publishing Company, Easton, Pa.

For example, the compounds useful in the invention may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, compounds useful in the invention may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of a compound useful in the invention. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

Cancer is a disease characterized in part by uncontrolled cell growth. Protein kinase C is directly involved in cellular growth control and is believed to be involved in tumor formation. Protein kinase C is the major, if not exclusive, intracellular receptor of phorbol esters which are very potent tumor promoters. Phorbol esters and other tumor promoters bind to and activate protein kinase C. Since diacylglycerol (DAG) and phorbol esters interact at the same site, DAG's have been suggested to be the "endogenous phorbol esters" by analogy with the opiate receptor where the conservation of a high affinity receptor implied the existence of an endogenous analogue. DAG has been shown to increase the affinity of protein kinase C for $Ca^{+2}$ and phospholipid and thus activates protein kinase C at cellular levels of these essential cofactors.

Extracellular signals including hormones, growth factors, and neurotransmitters are known to stimulate phosphatidylinositol turnover resulting in the generation of $IP_3$ and DAG. Structures of 40 distinct oncogenes of viral and cellular origin have revealed that oncogenes encode altered forms of normal cellular proteins. Several of the gene products appear related to growth factors or other elements involved in transmembrane signalling. These oncogene products appear to function by altering the level of critical second messengers. Cells transformed with the oncogenes ras, sis, erbB, abl, and src have been shown to contain elevated levels of DAG which is then believed to activate protein kinase C. Indeed, studies on ras transformed cells have shown protein kinase C activation to be concomitant with elevation of DAG.

Phorbol esters, such as phorbol myristate acetate (PMA), have complex effects on cells including effects on membrane function, mitogenesis, differentiation, and gene expression. Synthetic diacylglycerols mimic many of the effects of PMA in vitro and inhibitors of protein kinase C have been shown to block PMA-induced effects on cells. Thus, protein kinase C may mediate the actions of certain oncogenes, such as ras, which cause intracellular increases in DAG and concomitant increases in protein kinase C. In addition, activation of protein kinase C leads to the expression of c-myc, c-fos, c-cis, c-fms, nuclear protooncogenes important in cell transformation. Overexpression of protein kinase C in NIH 3T3 cells causes altered growth regulation and enhanced tumorigenicity and in rat fibroblasts leads to anchorage-independent growth in soft agar. In these experiments, overexpression of protein kinase C in these cells resulted in tumor formation in animals receiving transplanted cells.

Several studies have shown increased expression of protein kinase C in certain tumor types such as breast and lung carcinomas. Activated protein kinase C has also been detected in human colon carcinomas although increased expression on the gene level was not seen. Topoisomerases are directly modulated by protein kinase C as substrates for the enzyme and protein kinase C inhibitors have been shown to potentiate the action of chemotherapy drugs such as cis-platin. Other and more potent compounds which have been identified specifically as inhibitors of protein kinase C have shown early promise as therapeutic agents in inhibiting tumor growth in animal models.

Animal studies have shown that perhaps 50% or more of ischemic-related myocardial damage can be attributed to polymorphonuclear leukocytes (neutrophils) which accumulate at the site of occlusion. Damage from the accumulated neutrophils may be due to the release of proteolytic enzymes from the activated neutrophils or the release of reactive oxygen intermediates (ROI). Much of the "no reflow" phenomenon associated with myocardial ischemia is attributed to myocardial capillary plugging. The plugging of capillaries has been attributed to both aggregated platelets and aggregated neutrophils. Although both cell types are aggregated during the ischemic event, the relative contribution of each to capillary plugging has not yet been established. It is accepted that the damage by neutrophils to myocardial tissue proceeds through a cascade of events, one of the earliest being the bonding of activated neutrophils to damaged vascular endothelium. However, the binding of the neutrophils is significantly enhanced by their activation and this an even earlier event is the generation of molecules (such as cytokines, and chemotactic factors) which can function as activation stimuli. These molecules probably originate from damaged and aggregated platelets, from damaged vascular endothelium, or from the oxidation of plasma proteins or lipids by endothelial-derived oxidants.

Strategies for overcoming the deleterious effects of reactive oxygen intermediates have centered on the development of scavengers for the molecules. Superoxide dismutase (SOD) has been shown to be a particularly effective scavenger of superoxide, but suffers from a very short half-life in the blood. Several companies have tackled this problem by creating versions of this enzyme with increased half-lives by techniques such as liposome encapsulation or polyethylene glycol conjugation. Reports on the effectiveness of these new version are mixed. Catalase, a scavenger of hydrogen peroxide, and hydroxyl radical scavengers have also been tested and found to be effective to varying degrees. However, none of the strategies designed to scavenge reactive oxygen intermediates will prevent the aggregation of platelets, the release of chemotactic molecules, the activation and adherence of neutrophils to vascular endothelium, or the release of proteolytic enzymes from activated neutrophils.

One advantage of protein kinase C inhibitors as therapeutics for reperfusion injury is that they have been demonstrated to 1) block platelet aggregation and release of neutrophil activating agents such as PAF, 2) block neutrophil activation, chemotactic migration, and adherence to activated or damaged endothelium, and 3) block neutrophil release of proteolytic enzymes and reactive oxygen intermediates. Thus these agents have the capability of blocking all three of the most significant mechanisms of pathogenesis associated with reperfusion injury and should thus have a decided therapeutic advantage.

The 2-amino-1,3-diol group of sphingosine and dihydrosphingosine can adopt several stable conformations via intra-molecular hydrogen bonding. One of the hydroxyl oxygen molecules can adopt a conformation that allows it to hydrogen bond to another hydroxyl hydrogen to form a six-membered ring. Such hydrogen bonded ring structures are more stable than the non-bonded linear molecules.

The compounds useful in the present invention comprise molecular structures utilizing this added stability of a six-membered ring chair conformation by establishing covalent bonds in place of hydrogen bonding. Such molecules, 1,3 dioxanes, are conformationally rigid and should favor interactions with the protein kinase C and thereby improve enzyme inhibitory activities and subsequent biological effects of these compounds.

The compounds useful in the present invention may be synthesized by various approaches. Two approaches to the synthesis of the 1,3-dioxanes were investigated. The first approach involved the synthesis of a properly substituted 1,3 dioxane system which is illustrated in Scheme 1.

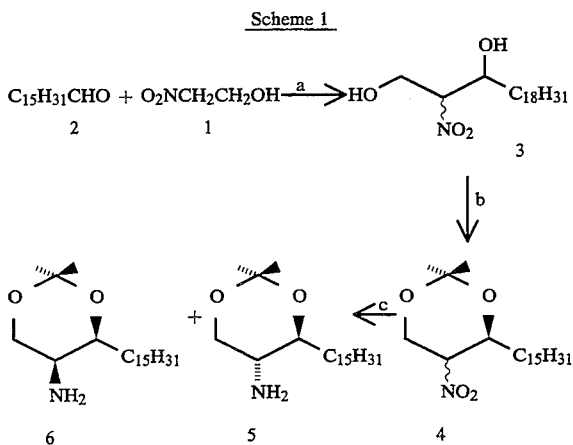

As shown in Scheme 1, functional 2-amino-1,3-diol groups were established in a single step employing the Henry Reaction. See Hass et al., Chem. Rev., 32: 406, 1943. Addition of the anion of 2-nitroethanol (1) to hexadecanal (2) gave 2-nitro-1,3-octadecanediol (3) as a mixture of threo- and erythro-isomers in moderate yield. These inseparable isomers were converted to isopropylidene (4) by treatment with 2-methoxypropene in methylene chloride at low temperature. The use of 2,2-dimethoxypropane as a reagent for acetalization required higher reaction temperature which led to the retroaldol reaction yielding starting compounds 1 and 2.

The nitro isopropylidene (4) proved to be easily epimerized to the more stable erythro isomer (5). Attempts to purify 4 on silica using flash column chromatography caused epimerization. Therefore, 4 was immediately reduced to the 5-amino-1,3-dioxane derivative with lithium aluminumhydride. Erythro- and threo-isomers (5 and 6, respectively) could be easily separated by flash column chromatography on silica.

Erythro- and threo-isomeric derivatives of the 5-amino-1,3-dioxanes (5 or 6) were prepared as shown in Scheme 2. For example, acetylation and amidination of 5 gave 7 and 10, respectively.

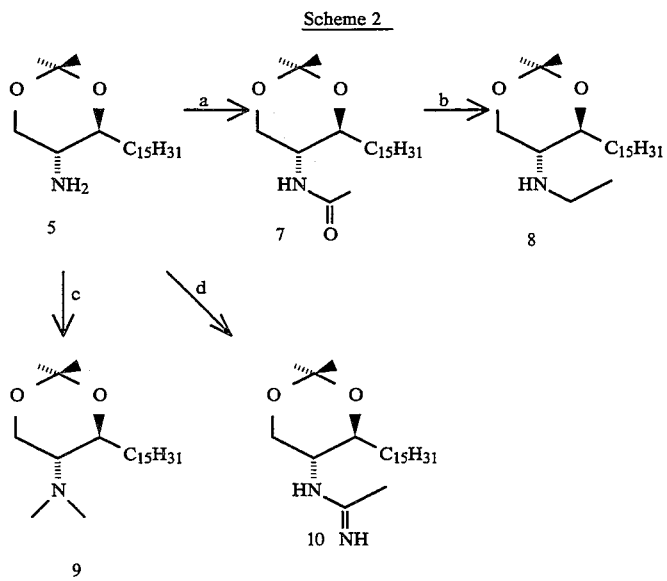

a) Ac$_2$O, py, CH$_2$Cl$_2$; 98%.
b) LAH, THF; 63%.
c) 37% formalin, NaBH$_3$CN, MeCN; 71%.
d) methyl acetimidate.

The optically active enantiomer of threo-5-amino-1,3-dioxane (6), (4S, 5S) threo-5-amino-4-pentadecyl-2,2-dimethyl-1,3-dioxane (13) was prepared as shown in Scheme 3. The pentultimate compound in the synthesis, (2S, 3S) threo-dihydrosphingosine N-t-butyl carbamate (12) was prepared from L-serine by the method of Garner et al., J. Org. Chem., 51: 2609, 1986.

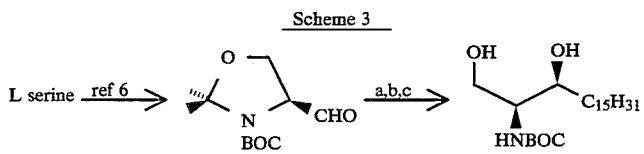

Scheme 3

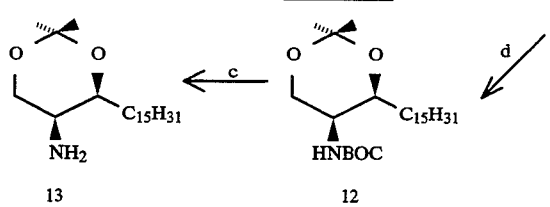

a) $C_{13}H_{27}C\equiv CLi$, $ZnBr_2$, $Et_2O$, $-78°$ C.; 77%.
b) Amberlyst-15, MeOH, RT; 67%.
c) 20% Pd on C, $H_2$, EtOAc; 100%.
d) 2-methoxypropene, p-TsOH, $CH_2Cl_2$; 68%.
e) TMSCl, NaI, MeCN; 18%.

The second synthetic approach to the 1,3-dioxane derivatives of the present invention employed compounds with established 2-amino-1,3-diol functionality as the starting point. One such example is shown in Scheme 4.

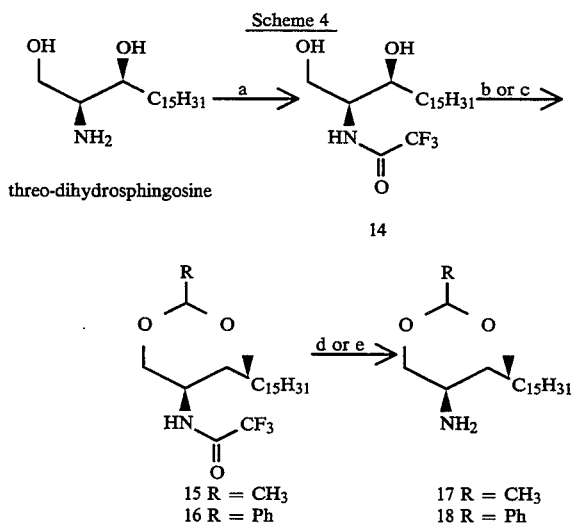

a) $CF_3CO_2Et$, $Et_3N$, MeOH; 96%.
b) $CH_2CHO$, p-TsOH, RT.
c) PhCHO, $ZnBr_2$, PhH, Δ.
d) R = $CH_3$; 15% NaOH, dioxane Δ; 26%.
e) R = Ph: $NaBH_4$, MeOH, RT; 15%.

The 2-monosubstituted 1,3-dioxanes were prepared from racemic threo-dihydrosphingosine, a known sphingolipid, by acetalization of the N-trifluoroacetyl protected derivative (14) with acetaldehyde and benzaldehyde, followed by deprotection to give 17 and 18 respectively.

The following nonlimiting examples illustrate a preferred embodiment for preparing the compounds of the invention shown in Table 1. The novel 1,3 dioxane derivatives of the invention may be prepared in a number of ways including those described above. The 1,3 dioxane derivatives of the invention may also be prepared by other methods known in the art, including synthetic and semi-synthetic techniques. As used herein, a 1,3 dioxane derivative structure has the conventional ring numbering as illustrated in the *Merck Index, Tenth Edition*, Merck & Co., Inc. Rahway, N.J., 1983, pp. 100-101.

EXAMPLE 1

Hexadecanal (2)

A solution comprising 10 g (85 mmole) of 1-hexadecanol in 100 ml of methylene chloride was added to a mixture comprising 10 g (139 mmole) of pyridinium chlorochromate, 30 g of celite and 12.0 g (146 mmole) of anhydrous sodium acetate in 400 ml of methylene chloride in a dropwise fashion. Following addition, the reaction mixture was stirred at room temperature for three hours then 300 ml of diethyl ether was added. The reaction mixture was filtered and a precipitate was collected and washed with diethyl ether until clear. The solvent was removed under reduced pressure and the residue passed through Florisil with diethyl ether as the eluent. The solvent was removed under reduced pressure and the residue purified by flash chromatography on silica (230 to 400 mesh) with hexanes and ethyl acetate at a ratio of approximately 39 to 1. The synthesis yielded hexadecanal having a mass of approximately 17.5 g and of approximately 88.4% purity. Hexadecanal is a white wax having a melting point of approximately 33°-34 C. The $^1$H NMR spectrum of the compound at 300 MHz using $CDCl_3$ comprised the following peaks: δ 0.892 (3H, t, J=6.5Hz), 1.267 (24H, bs), 1.61 to 1.66 (2H, m), 2.430 (2H, dt, J=1.7 and 7.3 Hz), and 9.776 (1H, s).

EXAMPLE 2

Threo/erythro-2-Nitro-1,3-octadecanediol (3)

A solution comprising 1.15 g (4.78 mmol) of hexadecanal and 0.5 g (5.49 mmole) of 2-nitroethanol in 20 ml of methanol was cooled to 0° C. 50 mg. (0.362 mmole) of potassium carbonate was added to the solution. The reaction mixture was stirred at 0° C. and gradually warmed to room temperature over three hours. 0.1 g (0.724 mmole) of potassium carbonate was again added and the reaction mixture stirred at room temperature overnight. The solvent was removed under reduced pressure. A remaining residue was taken up in 50 ml of ethyl acetate and washed twice with water in 25 ml portions. The organic layer was washed once with brine and dried over magnesium sulfate. The salts were filtered and the solvent removed under reduced pressure. A residue was purified by chromatography on silica (230 to 400 mesh) by gradient elution with hexanes at a ratio approximately between 3 to 1 and 2 to 1. This method yielded Threo/erythro-2-Nitro-1,3-octadecanediol having a mass of approximately 1.03 g and of approximately 85% purity. Threo/erythro-2-Nitro-1,3-octadecanediol is a white wax having a melting point of approximately 67°–71° C. The $^1$H NMR spectrum at 300 MHz using CDCl$_3$ comprised the following peaks: δ 0.890 (3H, t, J=6.3 Hz), 1.20 to 1.32 (26H, bs), 1.41 to 1.64 (2H, m), 2.32 to 2.59 (2H, m), and 4.09 to 4.63 (4H, m).

EXAMPLE 3

Threo- and erythro-2,2-Dimethyl-5-amino-4-pentadecyl-1,3-dioxane (5 and 6, respectively)

A solution comprising 13.3 g (40.3 mmole) of 2-nitro-1,3-octadecanediol in 300 ml of methylene chloride was cooled to −78° C. 0.5 g (2.63 mmole) of p-Toluenesulfonic acid monohydrate was added to the solution. A solution comprising 4.50 ml (47.0 mmole) of 2-methoxypropene in 100 ml of methylene chloride at 0° C. was added dropwise. After the addition was complete the reaction mixture was stirred at −78° C. for two hours, warmed to −40° C. for two hours, and then stirred at 0° C. for two hours. The reaction mixture was quenched at 0° C. The layers were separated and the organic layer was dried over magnesium sulfate. The salts were filtered and the solvent removed under reduced pressure. A residue having a mass of approximately 11.7 g was dissolved in 100 ml of anhydrous tetrahydrofuran and added dropwise to a 2.00 g (52.7 mmole) slurry of lithium aluminumhydride in 200 ml of tetrahydrofuran. After the addition was complete the reaction mixture was stirred at room temperature for 12 hours then refluxed for 4 hours. The reaction mixture was cooled to room temperature and quenched slowly and sequentially with 2.0 ml of water, 2.0 ml of a 15% aqueous solution of sodium hydroxide, followed by 6.0 ml of water. The reaction mixture was filtered and the precipitate was washed with diethyl ether. The filtrate was concentrated under reduced pressure and the residue purified by chromatography on silica (230 to 400 mesh) by gradient elution with hexanes and ethyl acetate at a ratio approximately between 9 to 1 and 1 to 1, and with 100% ethyl acetate. Purification yielded erythro-2,2-dimethyl-5-amino-4-pentadecyl-1,3-dioxane having a mass of approximately 1.45 g and of approximately 11% purity. Erythro-2,2-dimethyl-5-amino-4-pentadecyl-1,3-dioxane had a melting point of approximately 42.5° to 44.5° C. The $^1$H NMR spectrum at 300 MHz using CDCl$_3$ comprised the following peaks for the erythro isomer: δ 0.887 (3H, t, J=6.4 Hz), 1.263 (29H, bs), 1.394 (3H, s), 1.446 (3H, s), 1.69 to 1.73 (2H, m), 2.64 (1H, bs), 3.30 to 3.50 (2H, m), and 3.818 (1H, dd, J=5.3 and 11.3 Hz). An elemental analysis calculated for C$_{21}$H$_{43}$NO$_2$ comprised the following constituents: C: 73.84,H: 12.69, N: 4.10. The values obtained experimentally comprised: C: 73.67,H: 12.97, N: 4.04. The threo isomer comprised the following NMR peaks: δ 0.873 (3H, t, J=6.3 Hz), 1.249 (26H, bs), 1.398 (3H, s), 1.435 (3H, s), 1.637 (2H, bs), 2.474 (1H, d, J=1.6 Hz), 3.713 (1H, dd, J=1.2 and 11.7 Hz), 3.834 (1H, t, J=5.8 Hz), and 4.086 (1H, dd, J=1.9 and 11.7 Hz). Elemental analysis calculated for C$_{21}$H$_{43}$NO$_2$ comprised the following constituents: C: 73.84,H: 12.69, N: 4.10. The values obtained experimentally comprised: C: 73.55,H: 12.39, N: 3.88.

EXAMPLE 4

Erythro-N-Acetyl-5-amino-4-pentadecyl-1,3-dioxane (7)

0.25 ml (3.09 mmole) anhydrous pyridine was added to a solution of 0.2 g (0.586 mmole) erythro-5-amino-4-pentadecyl-1,3-dioxane and 0.25 g (2.65 mmole) acetic anhydride in 20 ml of methylene chloride. The reaction mixture was stirred at room temperature over night. The reaction mixture was extracted three times with 10 ml portions of 1N HCl and an organic layer was collected and dried over magnesium sulfate. Salts were removed by filtration and the solvent removed under reduced pressure. A residue was purified by chromatography on silica (230 to 400 mesh) with hexanes and ethyl acetate at a ratio of approximately 1 to 1 yielding erythro-N-Acetyl-5-amino-4-pentadecyl-1,3-dioxane having a mass of 0.22 g and of approximately 98.2% purity Erythro-N-Acetyl-5-amino-4-pentadecyl-1,3-dioxaneas is a white wax having a melting point of approximately 65° to 66.5° C. The $^1$H NMR analysis at 300 MHz using CDCl$_3$ comprised the following peaks: δ 0.890 (3H, t, J=6.6 Hz), 1.263 (31H, bs), 1.390 (3H, s), 1.428 (3H, s), 2.000 (3H, s), 3.48 to 3.55 (2H, m), 3.86 to 3.98 (2H, m), and 5.337 (1H, d, J=8.7 Hz).

EXAMPLE 5

Erythro-N-Ethyl-5-amino-4-pentadecyl-1,3-dioxane (8)

A solution comprising 50 g (0.130 mmole) of erythro-N-acetyl-5-amino-4-pentadecyl-1,3-dioxane in anhydrous 2 ml of tetrahydrofuran was added to a 50.0 mg (1.32 mmole) slurry of lithium aluminiumhydride in 3 ml of anhydrous tetrahydrofuran in a dropwise fashion. The reaction mixture was refluxed for four hours, cooled to room temperature, then quenched slowly and sequentially with 0.05 ml of water, 0.05 ml of a 15% aqueous solution of sodium hydroxide, and 0.15 ml of water. A precipitate was removed by filtration and washed with diethyl ether. A filtrate was concentrated under reduced pressure and the residue purified by chromatography on silica (230 to 400 mesh) with hexanes and ethyl acetate at a ratio of approximately 4 to 1. Purification yielded an oil, erythro-N-Ethyl-5-amino-4-pentadecyl-1,3-dioxane having a mass of approximately 30.2 mg and of approximately 62.7% purity. The $^1$H NMR spectrum of the compound at 300 MHz using CDCl$_3$ comprised the following peaks: δ 0.891 (3H, t, J=6.5 Hz), 1.096 (3H, t, J=7.1 Hz), 1.266 (26H, be), 1.388 (3H, s), 1.431 (3H, s), 2.44 to 2.57 (1H, m), 2.617 (1H, q, J=7.1 Hz), 2.690 (1H, q, J=7.1 Hz), 3.45 to 3.57 (2H, m), and 3.925 (1H, dd, J=5.0 and 11.4 Hz). Elemental analysis calculated for C$_{23}$H$_{47}$NO$_2$ comprised the following constituents: C: 74.73,H: 12.82, N: 3.79. The values obtained experimentally comprised: C: 74.80,H: 12.75, N: 3.71.

EXAMPLE 6

Erythro-5-N,N-Dimethylamino-4-pentadecyl-1,3dioxane (9)

0.17 g (2.71 mmole) of sodium cyanoborohydride was added to a solution comprising 0.1 g (0.293 g) of erythro-2,2-dimethyl-5-amino-4-pentadecyl-1,3-dioxane and 0.2 ml of a 37% aqueous solution of formaldehyde in 2.5 ml of acetonitrile in portions. After the addition was complete the reaction mixture was stirred at room temperature over night. The solvent was removed under reduced pressure and the residue taken up in ethyl acetate (10 ml) and water (10 ml). An aqueous layer was extracted three times with 10 ml portions of ethyl acetate. A combined organic layer was washed once with a 5% aqueous solutio of sodium hydroxide, once with brine, then dried over magnesium sulfate. Salts were removed by filtration and the solvent removed under reduced pressure. A residue was purified by chromatography on silica (230 to 400 mesh) with hexanes and ethyl acetate at a ratio of approximately 9 to 1 followed by hexanes and ethyl acetate at a ratio of approximately 1 to 1. Purification yielded an oil, erythro-5-N,N-Dimethylamino-4-pentadecyl-1,3-dioxane having a mass of 77.0 mg and of approximately 71.3% purity. The $^1$H NMR spectrum of the compound at 300 MHz using CDCl$_3$ comprised the following peaks: δ 0.847 (3H, t, J=6.5 Hz), 1.254 (29H, bs), 1.335 (3H, s), 1.394 (3H, s), 1.43 to 1.49 (2H, m), 2.326 (6H, s), 2.480 (1H, ddd, J=1.9, 5.5 and 6.3 Hz), 3.687 (1H, dt, J=1.9 and 8.9 Hz), and 3.78 to 3.85 (2H, m). Elemental analysis calculated for $C_{23}H_{47}NO_2$ comprised the following constituents: C: 74.73, H: 12.82, N: 3.79. The values obtained experimentally comprised: C: 74.67, H: 12.99, N: 4.06.

EXAMPLE 7

Erythro-5-Acetamidino-2,2-dimethyl-4-pentadecyl-1,3-dioxane (10)

A solution comprising 0.1 g (0.293 mmole) erythro-5-amino-4-pentadecyl-1,3-dioxane and 50 ml of methyl acetimidate in 50 ml of chloroform was stirred at room temperature for 3 days. The solvent was removed under reduced pressure and the residue purified by chromatography on silica (230 to 400 mesh) with chloroform increasing to chloroform and methanol at a ratio of approximately 3 to 1. Purification yielded erythro-5-Acetamidino-2,2-dimethyl-4-pentadecyl-1,3-dioxane having a mass of 60 mg and of approximately 53% purity. Erythro-5-Acetamidino-2,2-dimethyl-4-pentadecyl-1,3-dioxane is an off-white solid having a melting point of approximately 66° to 69° C. The $^1$H NMR spectrum of the compound at 300 MHz using CDCl$_3$ comprised the following peaks: δ 0.88 (3H, t, J=6.4 Hz), 1.25 (28H, bs), 1.39 (3H, s), 1.48 (3H, s), 2.34 (3H, s), and 3.63 to 3.82 (3H, m). IR (CCl$_4$): 2926, 2890, 1659, 1550, 1254, 1205, 1005, and 981 cm$^{-1}$. Elemental analysis calculated for $C_{23}H_{44}N_2O_2$ ¼ H$_2$O comprised the following constituents: C: 64.94, H: 11.60, N: 6.58. The values obtained experimentally comprised: C: 64.74, H: 11.20, N: 6.33.

EXAMPLE 8

Tert-Butyl (1S, 2S)-N-[2-hydroxy-1-(hydroxymethyl) heptadecyl]carbamate (11)

A solution comprising 2.49 g (6.08 mmole) of tert-Butyl (1S, 2S)-N-[2-hydroxy-1-(hydroxymethyl)-3-heptadecynyl]carbamate, Herold, Chim. Acta. 71: 354, 1988, and 20 mg of 20% Pd on carbon in 50 ml of ethyl acetate was hydrogenated on a Parr shaker at 3 atmospheres for 3 hours. The reaction mixture was filtered through Celite and the solvent removed under reduced pressure yielding tert-Butyl (1S, 2S)-N-[2-hydroxy-1-(hydroxymethyl) heptadecyl]carbamate having a mass of 2.53 g and of approximately 100%. Tert-Butyl (1S, 2S)-N-[2-hydroxy-1-(hydroxymethyl) heptadecyl]carbamate is a wax having a melting point of approximately 45° to 56° C. A $^1$H NMR analysis of the compound at 300 MHz using CDCl$_3$ comprised the following peaks: δ 0.887 (3H, t, J=6.7 Hz), 1.261 (26H, bs), 1.460 (9H, s), 2.054 (2H, bs), 3.589 (1H, bs), 3.820 (2H, bs), 3.941 (1H, bs) and 5.232 (1H, d, J=8.0 Hz). E;elemental analysis calculated for $C_{23}H_{47}NO_4$ comprised the following constituents: C: 68.78, H: 11.79, N: 3.49. The values obtained experimentally comprised: C: 68.46, H: 11.71, N: 3.44.

EXAMPLE 9

Threo-(2S, 3S)-N-tert-Butoxycarbonyl-5-amino-2,2-dimethyl-4-pentadecyl-1,3-dioxane (12)

0.1 g (0.526 mmole) of p-toluensulphonic acid was added to a solution comprising 0.5 g (1.24 mmole) of tert-Butyl (1S, 2S)-N-[2-hydroxy-1-(hydroxymethyl)-heptadecyl]carbamate in 20 ml of methylene chloride at 0° C. followed by 0.15 ml (1.57 Mole) of 2-methoxypropene. The reaction mixture was stirred at 0° C. for two hours then warmed to room temperature. The reaction mixture was extracted twice with 20 ml of a saturated aqueous solution of sodium bicarbonate in 20 ml portions and dried over magnesium sulfate. Salts were removed by filtration and the solvent removed under reduced pressure. A residue was purified by flash chromatography on silica (230 to 400 mesh) with hexanes and ethyl acetate at a ratio of approximately 9 to 1 to yield an oil, threo-(2S, 3S)-N-tert-Butoxycarbonyl-5-amino-2,2-dimethyl-4-pentadecyl-1,3-dioxane having a mass of approximately 0.287 g and of approximately 52% purity. The $^1$H NMR spectrum of the compound at 300 MHz using CDCl$_3$ comprised the following peaks: δ0.889 (3H, t, J=6.7 Hz), 1.261 (26H, bs), 1.460 (9H, s), 3.841 (1H, dd, J=1.4 and 9.8 Hz), 3.759 (1H, dd, J=1.4 and 11.8 Hz), 3.911 (1H, dt, J=1.3 and 6.5 Hz), 4.118 (1H, dd, J=1.5 and 11.8 Hz) and 5.232 (1H, d, J°8.0 Hz).

EXAMPLE 10

Threo-(2S, 3S) -5-Amino-2,2-dimethyl-4-pentadecyl-1,3 -dioxane ( 13 )

A solution comprising 0.28 g (0.634 Mole) of threo-(2S, 3S)-N-tert-butoxycarbonyl-5-amino-2,2-dimethyl-4-pentadecyl-1,3-dioxane, 0.25 ml (1.97 mmole) of chlorotrimethylsilane, and 0.3 g (2.0 mmole) of sodium iodide in 20 ml of anhydrous acetonitrile was stirred at room temperature over night. The solvent was removed under reduced pressure and a residue was taken up in 20 ml of methylene chloride. An organic layer was washed once with 10 ml of a saturated solution of aqueous sodium bicarbonate and then a 5% aqueous solution of sodium thiosulfate until clear. The organic layer was dried over magnesium sulfate. Salts were removed by filtration and the solvent removed under reduced pressure. A residue was purified by flash chromatography on silica (230 to 400 mesh) with sequential extractions with hexanes and ethyl acetate at a ratio between approximately 4 to 1, 3 to 1, 2 to 1 and 1 to 1. Purification yielded threo-(2S, 3S)-5-Amino-2,2-dimethyl-4-pentadecyl-1,3-dioxane having a mass of approximately 0.38 mg and of 18% purity. Threo-(2S, 3S)-5-Amino-2,2-dimethyl-4-pentadecyl-1,3-dioxane was a wax having a melting point of approximately 42.5° to 44.50° C. The $^1$H NMR spectrum of the compound at 300 MHz using CDCl$_3$ comprised the following peaks: δ0.873 (3H, t, J=6.3 Hz), 1.249 (26H, bs), 1.398 (3H, s), 1.435 (3H, s), 1.637 (2H, bs), 2.474 (1H, d, J=1.6 Hz), 3.713 (1H, dd, J=1.2 and 11.7 Hz), 3.834 (1H, t, J=5.8 Hz), and 4.086 (1H, dd, J=1.9 and 11.7 Hz). Elemental analysis calculated for $C_{21}H_{43}NO_2$ comprised the following constituents: C: 73.84, H: 12.69, N: 4.10. The values obtained experimentally comprised: C: 73.74, H: 12.61, N: 4.12.

EXAMPLE 11

Threo-N-Trifluoroacetyl-2-amino-1,3-octadecanediol (15)

1.20 ml (10.8 mmole) of ethyl trifluoroacetate and 2.0 ml (14.4 mmole) of triethylamine were added to a solution comprising 0.79 g (2.63 mmole) of threo-2-amino-1,3-octadecanediol in 25 ml of methanol. The reaction mixture was stirred at room temperature over night. The solvent was removed under reduced pressure and the residue was taken up in 30 ml of ethyl acetate. An organic layer was washed once with 20 ml of 0.5N hydrochloric acid and once with brine. The organic layer was dried over magnesium sulfate. Salts were removed by filtration and the solvent removed under reduced pressure to yield crude threo-N-Trifluoroacetyl-2-amino-1,3-octadecanediol having a mass of 0.11 g and of approximately 96% purity.

EXAMPLE 12

Threo-N-Trifluoroacetyl-5-amino-2-methyl-4-pentadecyl-1,3-dioxane (16)

A solution of 0.26 g (0.663 mmole) of threo-N-trifluoroacetyl-2-amino-1,3-octadecanediol and 10 mg of p-toluenesulphonic acid in 10 ml of acetaldehyde was stirred at room temperature over night. The solvent was removed under reduced pressure and the residue was taken up in ethyl acetate. An organic layer was washed twice with saturated aqueous solution of sodium bicarbonate in 10 ml portions and once with brine. The organic layer dried over magnesium sulfate. Salts were removed by filtration and the solvent removed under reduced pressure. A residue was purified by flash chromatography on silica (230 to 400 mesh) with hexanes and ethyl acetate at a ratio of approximately 9 to 1. Purification yielded an oil, threo-N-Trifluoroacetyl-5-amino-2-methyl-4-pentadecyl-1,3-dioxane having a mass of approximately 0.19 g and of 68% purity. The $^1$H NMR spectrum of the compound at 300 MHz using CDCl$_3$ comprised the following peaks: δ 0.881 (3H, t, J=6.9 Hz), 1.254 (28H, bs), 1.357 (3H, d, J=5.0 Hz), 3.75 to 3.80 (1H, m), 3.89 to 4.01 (2H, m), 4.774 (1H, q, J=5.0 Hz), and 6.901 (1H, d, J=8.1 Hz).

EXAMPLE 13

Threo-N-Trifluoroacetyl-5-amino-2-phenyl-4-pentadecyl-1,3-dioxane (17)

A solution comprising 0.26 (0.663 mmole) of threo-N-trifluoroacetyl-2-amino-1,3-octadecanediol, 0.1 g (0.734 mmole) of zinc chloride and 0.1 ml (0.984 mmole) of benzaldehyde in 25 ml of methylene chloride was stirred at room temperature over night. An organic layer was washed twice with a saturated aqueous solution of sodium bicarbonate in 10 ml portions and dried over magnesium sulfate. Salts were removed by filtration and the solvent removed under reduced pressure. A residue was isolated and used in the method of Example 14.

EXAMPLE 14

Threo-5-Amino-2-methyl-4-pentadecyl-1,3-dioxane (18)

A mixture comprising 0.1 (0.331 mmole) of threo-N-trifluoroacetyl-5-amino-2-methyl-4-pentadecyl-1,3-dioxane in 5 ml of a 15% aqueous solution of sodium hydroxide and 5 ml of 1,4-dioxane was refluxed for 8 hours. The solvent was removed under reduced pressure and the residue was taken up in methylene chloride. An organic layer was washed once with water and dried over magnesium sulfate. Salts were removed by filtration and the solvent removed under reduced pressure. The residue was purified by flash chromatography on silica (230 to 400 mesh) with ethyl acetate to yield threo-5-Amino-2-methyl-4-pentadecyl-1,3-dioxane having a mass of 70 mg and of 51% purity. Threo-5-Amino-2-methyl-4-pentadecyl-1,3-dioxane is a wax having a melting point of approximately 29° to 31° C. The $^1$H NMR spectrum of the compound at 300 MHz using CDCl$_3$ comprised the following peaks: δ0.864 (3H, t, J=6.7 Hz), 1.239 (28H, bs), 1.313 (3H, d, J=5.1 Hz), 2.490 (1H, ddd, apparent q, J=1.6, 1.6, and 1.8 Hz), 3.616 (1H, ddd, 1.6, 5.5, and 7.3 Hz), 3.854 (1H, dd, J=1.8 and 11.4 Hz), 3.947 (1H, dd, J=1.6 and 11.4 Hz), and 4.712 (1H, q, J=5.1 Hz). IR (neat): 2926, 2851, 1464, 1139, and 1106 cm$^{-1}$. Elemental analysis calculated for C$_{20}$H$_{41}$NO$_2$ comprised the following constituents: C: 73.33, H: 12.62, N: 4.28. The values obtained experimentally comprised: C: 73.22, H: 12.74, N: 4.19.

EXAMPLE 15

Threo-5-Amino-2-phenyl-4-pentadecyl-1,3-dioxane (19)

The residue from Example 14 was dissolved in 10 ml of methanol. To the solution was added 0.1 g (2.64 mmole) of sodium borohydride in portions. The reaction mixture was stirred at room temperature over night. The solvent was removed under reduced pressure and the residue taken up in ethyl acetate. An organic layer was washed with water and dried over magnesium sulfate. Salts were removed by filtration and the solvent removed under reduced pressure. A residue was purified by flash chromatography on silica (230 to 400 mesh) with hexanes and ethyl acetate at a ratio of approximately 1 to 1 then in 100% ethyl acetate to yield threo-5-Amino-2-phenyl-4-pentadecyl-1,3-dioxane having a mass of approximately 12 mg and of approximately 15% purity. Threo-5-Amino-2-phenyl-4-pentadecyl-1,3-dioxane is a wax having a melting point of approximately 41° to 43° C. The $^1$H NMR spectrum of the compound at 300 MHz using CDCl$_3$ comprised the following peaks: δ 0.887 (3H, t, J=6.7 Hz), 1.227 (26H, bs), 2.633 (1H, ddd, J=1.5, 1.6, and 2.0 Hz), 3.878 (1H, ddd, 1.6, 5.0, and 5.4 Hz), 4.094 (1H, dd, J=2.0 and 11.4 Hz), 4.159 (1H, dd, J=1.5 and 11.4 Hz), and 7.30 to 7.55 (5H, m). The infrared spectrum IR (neat) comprised the following peaks: 2952, 2918, 2849, 1470, and 1024 cm$^{-1}$. Elemental analysis calculated for C$_{25}$H$_{43}$NO$_2$ ¼ H$_2$O comprised the following constituents: C: 76.19, H: 11.12, N: 3.55. The values obtained experimentally comprised: C: 76.38, H: 11.05, N: 3.36.

Table I illustrates chemical compositions and moieties of 1,3 dioxane derivatives of Formula I. Moieties of 1,3 dioxane derivatives are designated by the symbols "R$_1$" through "R$_6$" and are listed in the columns labeled by these symbols. The approximate melting point of a compound in degrees centigrade is indicated in the column labeled "mp(°C.)."

TABLE 1

| Compound | R$^1$ | R$^2$ | R$^3$ | R$^4$ | R$^5$ | R$^6$ | mp(°C.) |
|---|---|---|---|---|---|---|---|
| 5 | C$_{15}$H$_{31}$ | CH$_3$ | CH$_3$ | H | H | | 39–41 |
| 6 | C$_{15}$H$_{31}$ | CH$_3$ | CH$_3$ | H | H | | 42.5–44.5 |
| 13 | C$_{15}$H$_{31}$ | CH$_3$ | CH$_3$ | H | H | | 42.5–44.5 |
| 10 | C$_{15}$H$_{31}$ | CH$_3$ | CH$_3$ | R$_6$(NH=)C | H | CH$_3$ | 66–69 |
| 18 | C$_{15}$H$_{31}$ | CH$_3$ | H | H | H | | 29–31 |
| 19 | C$_{15}$H$_{31}$ | Ph | H | H | H | | 41–43 |
| 20 | C$_{13}$C=C | CH$_3$ | H | H | H | | |
| 21 | C$_{15}$H$_{31}$ | C$_{14}$H$_{29}$ | H | H | H | | |
| 22 | C$_{15}$H$_{31}$ | C$_6$H$_{13}$ | H | H | H | | |
| 23 | C$_{15}$H$_{31}$ | CH$_3$ | H | R$^6$C(=NH) | H | C$_2$H$_5$ | |
| 24 | C$_{15}$H$_{31}$ | H | H | H | H | | 32–33 |
| 25 | C$_{13}$CH=CH | H | C$_{20}$H$_{41}$ | NH$_2$(NH=)C | H | | |

In Table I, Ph = Phenyl.

EXAMPLE 16

Protein Kinase C Inhibition

A protein kinase C (PKC) assay is designed to duplicate the in vivo conditions required for protein kinase C function. Therefore, pH, salt and cofactor concentrations are similar to physiologic levels. A lysine rich histone, H1, was used in the assay as the phosphorylation acceptor-protein because it is readily available and serves as a good substrate for protein kinase C. Enzyme was prepared from rat brain and purified to apparent homogeneity as determined by a single band on silver stained SDS-polyacrylamide.

In the screening assay, phosphatidylserine (PS) and DAG were co-sonicated to form unilamellar and multilamellar vesicles. The concentration of lipids in the assay were suboptimal to maximize the detection potential of the assay for inhibitors. Potential inhibitor compounds were added to the assay in dimethylsulfoxide at three concentrations to give final inhibitor concentrations of 4.3, 43 and 218 μM, respectively. The assay was started with the addition of enzyme and stopped after 10 min by the addition of 25% trichloroacetic acid (TCA) and 1.0 mg/ml bovine serum albumin (BSA). The radioactive histone product was retained and washed on glass fiber filters that allow the unreacted $^{32}$p-ATP to pass through. The amount of phosphorylation was determined by the radioactivity measured in a scintillation counter. Controls were included in every assay to measure background activity in the absence of enzyme, activity in the absence of lipids, and the maximum enzyme activity with saturating levels of the activator lipids. Table 2 shows the protein kinase C assay components and their concentrations.

TABLE 2

| Assay Component | Concentration |
|---|---|
| HEPES pH 7.5 | 20 μM |
| MgCl$_2$ | 20 μM |
| CaCl$_2$ | 100 μM |
| EGTA | 95 μM |
| Histone H1 | 200 μg/ml |
| Phosphatidylserine | 40 μg/ml |
| Diacylglycerol | 1.8 μg/ml |
| Protein Kinase C | 0.6 μg/ml |
| γ-$^{32}$P-ATP | 20 μM |

HEPES is N-[2-hydroxyethyl] piperizine-N'-[ethanesulfonic acid] and EGTA Ethylene-bis (oxyethylenenitrilo) tetraacetic acid.

Results of the protein kinase C assay are shown in Table 3 in the column labeled PKC. Results are shown as IC$_{50}$, which is the concentration of test compound needed to inhibit 50% of the protein kinase C activity as compared with levels of protein kinase C activity in controls. Compounds of the invention were able to effectively inhibit protein kinase activity.

TABLE 3

| Compound | IC$_{50}$(μM) PKC |
|---|---|
| 5 | 130 |
| 6 | 120 |
| 10 | 29 |
| 13 | 121 |
| 18 | 64 |
| 19 | 182 |
| 24 | 83 |

EXAMPLE 17 cAMP (Dependent Protein Kinase (PKA) Assay

Compounds found to be inhibitors of protein kinase C were tested for inhibitory activity against cAMP dependent protein kinase (PKA). This enzyme, like protein kinase C, plays an important role in cell-cell communication and is activated by a second messenger, cAMP. Secondary screening against PKA is useful for ascertaining the selectivity of the compounds of the invention. The standard assay conditions are given in Table 4. The catalytic subunit of PKA (Sigma Chemical Company, St. Louis, Mo.) was mixed with buffer before addition of the inhibitor in dimethylsulfoxide (DMSO). Potential inhibitor compounds were added to the assay in dimethylsulfoxide at three concentrations to give final inhibitor concentrations of 4.3, 43 and 218 μM, respectively. The assay was started by the addition of 32P-ATP and the reaction was allowed to proceed for 10 min before stopping with 25% trichloroacetic acid (TCA) and 1.0 mg/ml bovine serum albumin (BSA). Phosphorylated protein was then isolated by filtration and the radioactivity was counted in a beta scintillation counter.

TABLE 4

| Assay Components | Concentration |
|---|---|
| HEPES pH7.5 | 20 μM |
| Histone H1 | 200 μg/ml |
| Dithiothreitol | 32 μg/ml |
| Protein Kinase A | 2.6 μg/ml |
| γ-$^{32}$-ATP | 20 μM |

Compounds 5, 6, 10, 13, 18, and 19 were tested in PKA assays but had no effect on PKA activity. Thus, the tested compounds of the invention are selective for protein kinase C, and have no effect on cAMP dependent protein kinase. The compounds of the invention should thus have no effect on the metabolic pathways associated with stimulation of protein kinase by cAMP.

EXAMPLE 18

Human Tumor Cell Growth Inhibition

MCF-7 a human breast tumor cell line and MCF-7/ADR an adriamycin resistant line of MCF-7 cells were obtained from the National Cancer Institute, Frederick, Md. CEM cells (ATCC accession number CCL 119) were obtained from the American Type Culture Collection, Rockville, Md.

Human tumor cells were trypsinized with 0.05% trypsin (GIBCO), counted with a hemacytometer and seeded at a concentration of 10,000 cells/well in a 96 well microtiter plate. After allowing cells to attach to the surface overnight, the culture medium was aspirated and replaced with 100 $\mu$l of fresh medium. Test agents were diluted to determine dose response at 2X final concentration and added in quadruplicate at 100 $\mu$l/well to bring the total volume of each well to 200 $\mu$l. The microtiter plate was then incubated at 37° C. 5% $CO_2$ overnight for 18 to 24 hrs before $^3$H-thymidine was added at a concentration of 0.5 $\mu$Ci/well in 50 $\mu$l culture medium. The plate was incubated again for 4 hrs under the same conditions as above. Supernatant was then aspirated and 50 $\mu$l of 0.05% trypsin (GIBCO) was added to each well.

Cells were checked microscopically to determine detachment from surfaces, and plates were then harvested with a cell harvester (PHD, Cambridge Technology, Inc.) Filter papers corresponding to wells were placed in scintillation vials and counted to determine the amount of $^3$H-thymidine incorporated by the cells. Test agent response was compared to a positive control of cell wells with culture media only to determine the $IC_{50}$. $IC_{50}$ is the concentration of test compound required to inhibit fifty percent of the incorporation of $^3$H-thymidine into proliferating cells not exposed to test agent. Uptake of 3H-thymidine is a standard test for measuring the metabolism of cells. Cells which are actively proliferating take up $^3$H-thymidine whereas cells that are not proliferating take up $^3$H-thymidine at much slower rates or not at all. Test agents that inhibit the uptake of $^3$H-thymidine thus slow the growth of cells.

As shown in Table 5, compounds of the invention were able to inhibit $^3$H-thymidine uptake and thus inhibit the proliferation of the tested cell lines. When tested with cell line MCF-7, compound 5 had an $IC_{50}$ of 7.7 $\mu$M. However, when tested with MCF-7/ADR, the $IC_{50}$ of the compound was 6.6. The results with the compounds 6 and 13 were similar. When tested with MCF-7 cells, the $IC_{50}$ was 6.0 $\mu$M and 5.1 $\mu$M respectively, however the $IC_{50}$ was 5.5 $\mu$M and 6.3 $\mu$M when compounds 6 and 13 were tested with cell line MCF-7/ADR. Thus compounds useful in the invention not only inhibit tumor cell proliferation but are not cross-resistant to the multi-drug-resistant family of agents such as adriamycin.

TABLE 5

| Compound | $IC_{50}$ ($\mu$M) MCF-7 | MCF-7/ADR |
|---|---|---|
| 5 | 7.7 | 6.6 |
| 6 | 6.0 | 5.5 |
| 11 | 3.2 | |
| 13 | 5.1 | 6.3 |

EXAMPLE 19

Human Keratinocyte Inhibition

Proliferating keratinocytes (NHEK cells purchased from Clonetics, Inc., San Diego, Calif.) in second passage were grown in Keratinocyte Growth Medium (KGM) (Clonetics, Inc.) Cells were trypsinized (0.025% trypsin, Clonetics), counted with a hemacytometer (Scientific Products), and seeded at a concentration of 2,500 cells/well in a 96 well microtiter plate. After allowing cells to attach to the surface overnight, the culture medium was aspirated and replaced with 100 $\mu$l of fresh KGM. Test agents were evaluated and $IC_{50}$'s were determined according to the $^3$H-thymidine incorporation procedures described as in Example 18. $IC_{50}$ is the concentration of test compound required to inhibit fifty percent of the incorporation of $^3$H-thymidine into proliferating cells not exposed to test agent.

TABLE 7

| Compound | $IC_{50}$ ($\mu$M) |
|---|---|
| 3 | 6.5 |
| 6 | 4.7 |
| 11 | 0.8 |

As shown in Table 7, these results indicate that compounds of the invention were active against human keratinocytes, and will be useful in treating topical inflammatory conditions such as psoriasis and other conditions where hyperproliferation of keratinocytes is a symptom.

EXAMPLE 20

Neutrophil Superoxide Anion ($O_2$—) Release Assay

Neutrophils were isolated form whole blood collected from human volunteers. All reagent materials are obtained from Sigma Chemical Company with the exception of isotonic saline (Travenol Laboratories, Inc., Deerfield, Ill.) and lymphocyte separation medium (Organon Teknika, Durham, N.C.).

Neutrophil Isolation

Whole blood was drawn and mixed with sodium heparin to a final concentration of 10 units/ml to prevent clotting. An equal volume of 3.0 % dextran in isotonic saline was added, mixed, and allowed to settle for 30 minutes to bind red blood cells (RBC). Supernatant was removed, underlayered with lymphocyte separation medium and centrifuged for 40 min at 400 xg in a centrifuge (Beckman GPR, Norcross, Ga.). The pellet was alternately taken up in 0.2% and 1.6% NaCl to lyse RBCs before washing with Hank's Balanced Salt Solution (HBSS). The washed pellet was resuspended in 10 ml HBSS and placed on ice before counting on a hemacytometer.

Assay Procedure

The neutrophil cell concentration was adjusted to $2\times10^6$ cells/ml with HBSS before adding 0.8 ml cells to $12\times75$ mm polypropylene test tubes (Fisher Scientific). Test agents were diluted to determine dose response and added at 10X final concentration at a volume of 0.1 ml/tube in duplicate. Then 10X concentrations of cytochrome C (15 mg/ml) with catalase (3000 units/ml) either alone or containing 25 ng/ml phorbol 12-myristate 13-acetate (PMA) were added at a volume of 0.1 ml/tube and incubated at 37° C. for 30 minutes before stopping the reaction by placing tubes on ice. Tubes were then centrifuged at 900 xg for 10 minutes and 0.5 ml supernatant was removed and added to 0.5 ml $H_2O$ in a microcuvette. Optical density (OD) of cytochrome c was read in a spectrophotometer (Shimadzu) at 550 nm. The $\Delta$OD of cytochrome c was obtained between PMA-stimulated and non-stimulated tubes, and the dose responses of the test agents were compared to the positive controls which contain HBSS in place of test agents. PMA stimulates $O_2^+$ production which reduces cytochrome c. Reducing cytochrome c increases its absorbance, and the change in OD of cytochrome c is proportional to the amount of $O_2^+$ produced by PMA stimulation. Inhibition of the $O_2^+$ burst by test compounds of the invention is seen as a reduction in the change in optical density. Inhibition is expressed as $IC_{50}$ $\mu$M and is the amount of test compound that will inhibit fifty percent of the PMA-stimulated respiratory outburst, i.e. $O_2^+$ production.

The tested compounds that were able to inhibit $O_2^+$ production by PMA-stimulated neutrophils are shown in Table 8.

TABLE 8

| Neutrophil Superoxide Release | |
|---|---|
| Compound | $IC_{50}$ ($\mu$M) |
| 5 | 13.10 |
| 6 | 9.04 |
| 10 | 1.52 |
| 13 | 2.40 |

We claim:

1. A compound having the formula

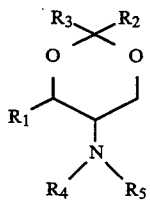

wherein $R_1$ is alkyl, alkenyl or alkynyl having from 2 to about 20 carbon atoms; $R_2$, $R_3$, $R_6$ are independently H, phenyl or alkyl having from 1 to about 20 carbon atoms; $R_4$ is H; and $R_5$ is $R_6$imino or amidino; or a pharmaceutically acceptable salt thereof.

2. The compound of claim 1 wherein $R_1$ has from about 10 to about 20 carbon atoms; and $R_2$, $R_3$ and $R_6$ are independently H or alkyl having from 1 to 5 carbon atoms.

3. The compound of claim 1 wherein $R_1$ has from about 15 to about 20 carbon atoms; and $R_2$, $R_3$ and $R_6$ are independently H, methyl or ethyl; and $R_5$ is $R_6$imino.

4. A compound having the formula

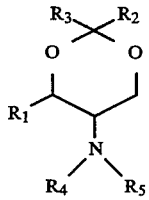

wherein $R_1$ is alkyl, alkenyl or alkynyl having from 2 to about 20 carbon atoms; $R_2$ is alkyl having from 1 to about 5 carbon atoms; $R_3$ is H; $R_4$ is H; $R_5$ is $R_6$imino or amidino; and $R_6$ is H, phenyl or alkyl having from 1 to about 20 carbon atoms; or pharmaceutically acceptable salt thereof.

5. The compound of claim 4 wherein $R_1$ has from about 10 to about 20 carbon atoms.

6. The compound of claim 5 wherein $R_1$ has from about 15 to about 20 carbon atoms.

7. A compound having the formula

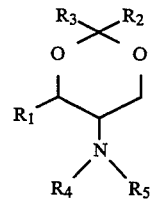

wherein $R_1$ is alkyl, alkenyl or alkynyl having from 2 to about 20 carbon atoms; $R_2$ is alkyl having from 7 to about 20 carbon atoms; $R_3$ is H; $R_4$ is H; $R_5$ is $R_6$imino or amidino; and $R_6$ is H, phenyl or alkyl having from 1 to about 20 carbon atoms; or a pharmaceutically acceptable salt thereof.

8. The compound of claim 7 wherein $R_1$ has from about 10 to about 20 carbon atoms.

9. The compound of claim 8 wherein $R_1$ has from about 15 to about 20 carbon atoms; and $R_5$ is $R_6$imino.

10. A pharmaceutical composition comprising a pharmaceutically acceptable carrier or diluent and a compound having the formula

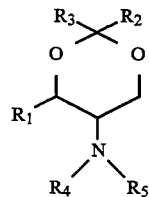

wherein $R_1$ is alkenyl or alkynyl having from 2 to 14 carbon atoms; $R_2$ is phenyl; $R_3$ and $R_6$ are independently H, or alkyl having from 1 to about 20 carbon atoms; $R_4$ is H; and $R_5$ is $R_6$imino or amidino; or a pharmaceutically acceptable salt thereof.

11. A pharmaceutical composition comprising a pharmaceutically acceptable carrier or diluent and a compound having the formula

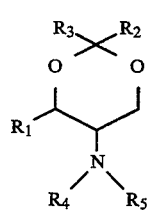

wherein $R_1$ is alkyl, alkenyl and alkynyl having from 2 to 20 carbon atoms; $R_2$ and $R_3$ are independently H or alkyl having from 1 to about 20 carbons; $R_4$ is H; $R_5$ is $R_6$imino or amidino; and $R_6$ is H, phenyl or alkyl having from 1 to about 20 carbon atoms; or pharmaceutically acceptable salt thereof.

12. The pharmaceutical composition of claim 11 wherein $R_1$ has from about 10 to about 20 carbon atoms;

$R_2$ and $R_3$ are independently H or alkyl having from 1 to about 5 carbons; $R_6$ is H, phenyl or alkyl having from 1 to about 5 carbon atoms.

13. The pharmaceutical composition of claim 11 wherein $R_1$ has from about 15 to about 20 carbon atoms; $R_2$, $R_3$ and $R_6$ are independently H, methyl or ethyl; and $R_5$ is $R_6$imino.

14. A pharmaceutical composition comprising a pharmaceutically acceptable carrier or diluent and a compound of claim 1.

15. A pharmaceutical composition comprising a pharmaceutically acceptable carrier or diluent and a compound of claim 2.

16. A pharmaceutical composition comprising a pharmaceutically acceptable carrier or diluent and a compound of claim 3.

* * * * *